United States Patent [19]

Meiller et al.

[11] 4,132,596

[45] Jan. 2, 1979

[54] SUPPORT-AMINOACYLASE COMPLEXES

[75] Inventors: François Meiller, Palaiseau; Bernard Mirabel, Fresnes, both of France

[73] Assignee: Rhone Poulenc Industries, Paris, France

[21] Appl. No.: 799,117

[22] Filed: May 20, 1977

[30] Foreign Application Priority Data

May 26, 1976 [FR] France .................. 76 15984

[51] Int. Cl.² ............................................. C07G 7/02
[52] U.S. Cl. ........................................ 195/63; 195/29; 195/68; 195/DIG. 11
[58] Field of Search .............. 195/29, 63, 68, DIG. 11

[56] References Cited

U.S. PATENT DOCUMENTS

| | | | |
|---|---|---|---|
| 3,705,084 | 12/1972 | Reynolds .................. | 195/63 |
| 3,796,634 | 3/1974 | Haynes et al. ............ | 195/63 |
| 3,915,797 | 10/1975 | Ishimatsu et al. ........ | 195/63 |
| 4,034,139 | 7/1977 | Mazarguil et al. ........ | 195/68 X |

Primary Examiner—David M. Naff
Attorney, Agent, or Firm—McDougall, Hersh & Scott

[57] ABSTRACT

Aminoacylase is absorbed on a porous inorganic support that has been coated with a film of cross-linked polymer containing tertiary amine or quaternary ammonium salt groups to provide support-aminoacylase complexes for use in the separation of racemic acetylaminoacids.

8 Claims, No Drawings

SUPPORT-AMINOACYLASE COMPLEXES

The present invention concerns support-aminoacylase complexes, as well as their use in separating of racemic, acetylamino-acids.

In order to carry out this separation reaction, various support-enzyme complexes have been proposed. These are for example complexes in which the enzyme is fixed by a covalent bond to the support consisting of a polymer, but the said complexes progressively lose their activity during use and it is impossible to regenerate them.

There are also complexes in which the enzyme is adsorbed on a support consisting of a polysaccharide to which are fixed quaternary ammonium or tertiary amines. However, these complexes do not have desirable mechanical properties and are consequently difficult to use in a column, unless it is operated under very special conditions, and this is even more so if the reaction is carried out under pressure; their volume undergoes changes with the ionic strength or the pH of the medium. Furthermore, they are biodegradable and cannot be heat sterilized.

The support-aminoacylase complexes of the invention do not have these disadvantages; they possess very good mechanical properties, and may therefore be used in a column, even under pressure; their volume does not undergo change; they are not biodegradable and may be sterilized. Moreover, they lose their activity only extremely slowly and may be regenerated very simply.

The complexes according to the invention are enzymatically active, stable products consisting of aminoacylase adsorbed on a support, and characterized in that the support is a porous mineral substance having a grain size between 4 μm and 5 mm, a specific surface of the order of 5 to 150 m²/g, a pore diameter of 500 to 2500 Å, a pore volume of 0.4 to 2 ml/g, and coated, in an amount of less than 10 mg/m², with a film of cross-linked polymer containing or bearing tertiary amine or quarternary ammonium salt groups.

As porous mineral support, forming part of the composition of the complexes, there may be mentioned metal oxides such as: titanium oxide, aluminas, and more especially silicas. These supports have average pore diameters of 500 to 2500 Å and preferably 600 to 1500 Å, a specific surface of 5 to 150 m²/g and preferably 20 to 50 m²/g, a grain size of 4 μm to 5 mm, and a pore volume of 0.4 to 2 ml/g.

The functional groups, i.e. tertiary amines or quaternary ammonium salts, are represented by the general formulae

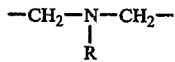

or —CH$_2$— N$^{(\pm)}$(R)$_3$ X$^{(-)}$, in which R, which may be identical or different, represents an alkyl or hydroxyalkyl group having 1 to 4 carbon atoms and X represents an inorganic or organic anion, such as for example chloride, sulphate, nitrate, phosphate and citrate.

These functional groups form part of the chain of the cross-linked polymer, or are fixed to the cross-linked polymer which covers the entire surface of the support.

The cross-linked polymers, which cover the surface of the inorganic support, are products known per se, obtained by any conventional polymerization processes. They are prepared from monomers capable of cross-linking between themselves, or with another monomer (copolymers), if necessary in the presence of a catalyst. Among these monomers there may be mentioned: epoxide compounds which cross-link with polyamines as catalysts; polyamine-formaldehyde and phenol-formaldehyde mixtures, which cross-link without a catalyst; mixtures of vinyl monomers, e.g. vinylpyridine-ethyleneglycol diacrylate, vinylpyridine-vinyltriethoxysilane, styrene-divinylbenzene, and styrene-vinyltriethoxysilane, which cross-link with an initiator which liberates free radicals, such as organic peroxides and azonitriles.

In the case where the cross-linked polymer on the surface of the inorganic support does not have the functional groups, such as defined above in its chain, it is necessary to modify the said polymer by any process known per se.

In the coating operation of the inorganic support, the amount of monomer(s) to be used should be such that the amount of cross-linked polymer having functional groups and distributed on the surface of the inorganic support should be less than 10, and preferably between 1 and 6 mg/m², so as to form a film which does not block the pores of the support.

The inorganic supports coated with cross-linked polymers having functional groups thus obtained, have an exchange capacity of less than 2 meq/g and preferably between 0.3 and 1.2 meq/g.

The aminoacylases adsorbed on the support are enzymes which may be of animal origin, for example extracted from pigs' kidneys, or even produced by microorganisms such as Aspergillus, *Lactobacillus Arabinosus*, *Micrococus Glutamicus*, and *Pseudomonas Crucivine*.

The fixation of the enzyme on the support is effected in a manner known per se, in the cold and in buffered or unbuffered aqueous solution, adjusted to the pH value most compatible with the enzyme, either by simple contact for the time necessary for the fixation or by passing the enzyme solution over the support contained in a column.

The enzymes thus fixed are stable and active, and their relative activity is a function of the nature and origin of the enzyme.

The object of the invention is also the use of aminoacylase-support complexes for the separation of racemic acetylamino-acids.

Of the acetylamino-acids which may be treated by the complexes of the invention, there may be mentioned: N-acetyl-DL-arginine, N-acetyl-DL-histidine, N-acetyl-DL-valine, N-acetyl-DL-tryptophan, N-acetyl-DL-alanine, N-acetyl-DL-leucine, N-acetyl-DL-tyrosine, N-acetyl-DL-phenylalanine, N-acetyl-DL-methionine and N-acetyl-DL-CH$_2$O$_2$ dopa.

The conversion of the N-acetylamino-acid into L-amino-acid is obtained by contacting an aqueous solution of the DL amino-acid with the complex for the time necessary for the conversion, or, preferably by passing the said solution through a column containing the complex. The concentration of acetylamino-acid in the solution is of the order of 0.1 to 2 moles/liter; the pH compatible with the enzyme is between 6 and 10, and the temperature is between ambient temperature and 65° C.

When the conversion is carried out in a column, the linear flow velocity is between 0.1 and 30 cm/minute. A high linear velocity, that is to say greater than a few cm/minute enables the productivity greatly to be raised, but creates a certain pressure in the column. This pressure is not a disadvantage however, since it does not affect the volume of the complex, due to the mechanical properties of the latter. This is not the case with complexes of the prior art.

Depending on the origin of the enzyme used, it may be advantageous, in order to accelerate the reaction, to add a small amount of an activator to the amino-acid solution, for example cobalt ions in an amount of between $10^{-2}$ and $10^{-5}$ mole/l, in the form of a salt, such for example as the chloride.

The L-amino-acid obtained is separated by any known method, such as precipitation or chromatographic techniques.

The complexes according to the invention are relatively stable. However, after prolonged use, for example 30 days, the complex becomes exhausted. This is not a disadvantage however, since in order to regenerate the complex it is sufficient simply to contact the exhausted support once again with a solution of the enzyme.

Examples of embodiments of the invention are given hereinafter by way of illustration and not by way of limitation.

EXAMPLE 1

Fixation of the Enzyme

The support used consists of a silica having a grain size of 40–100 μm, a specific surface of 37 m²/g, a pore diameter of 1100 Å, and a pore volume of 0.97 ml/g, coated with a cross-linked polymer containing

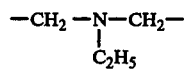

functional groups. The support has the following characteristics:
  carbon content: 8.8%
  nitrogen content: 2.4%
  amount of fixed polymer: 3.3 mg/m²
  exchange capacity: 1 meq/g 6 ml of the support, i.e. 3 g, are added to a column 1 cm in diameter, 40 ml of a 0.5% by weight solution in distilled water of L-aminoacylase extracted from pigs' kidneys is passed through the column at a flow rate of 120 ml/h.

The support on which the enzyme is adsorbed is washed by passing 50 ml of distilled water through the column at a flow rate of 120 ml/h.

The support-enzyme complex obtained has an activity of 40 units per gram of complex, a unit being the number of micromoles of L-amino-acid obtained per minute at 55°.

Separation of L-methionine

An aqueous solution of 0.1 M N-acetyl-DL-methionine, containing $5 \times 10^{-4}$ M of Co$^{++}$ ions, at a pH of 7 and a temperature of 55° C., is passed through the column at a rate of 60 ml/h.

The concentration of L-methionine in the effluent is determined by the ninhydrin reaction. It is found that the conversion rate is 92 mole % after 3 hours' operation.

EXAMPLE 2

Fixation of the Enzyme

A support consisting of silica having a grain size of 100–200 μm, a specific surface of 24 m²/g, a pore diameter of 1400 Å, and a pore volume of 1,1 ml/g, and coated with a styrene-based cross-linked polymer having the functional groups

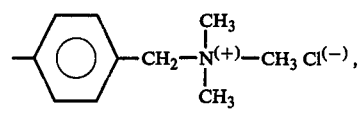

is used; the support has the following characteristics:
  carbon content: 4.8%
  chlorine content: 2%
  nitrogen content: 0.9%
  amount of fixed polymer: 3.3 mg/m²
  exchange capacity: 0.5 meq/g 3 g of the support are contacted for 1 hour with 100 ml of a 0.5% by weight solution in distilled water of the same L-aminoacylase as in example 1, the pH being adjusted to 7.

The support-enzyme complex formed is then separated by filtration, and washed with distilled water. Its activity is 45 units/g.

Separation of L-methionine

The complex is added to a column identical to that of example 1, through which a solution of N-acetyl-DL-methionine is passed under the same conditions as in Example 1.

The molar conversion rate is 100%.

EXAMPLE 3

Fixation of the Enzyme 20 ml, i.e. 10 g of the same support as in example 2, is added to a column 2.5 cm in diameter, 150 ml of a 1% solution in distilled water of L-aminoacylase obtained from Aspergillus and marketed under the brand name AMANO (Pharmaceutical Co. Ltd.), is passed through the column in 1 hour.

The support-enzyme complex is washed by passing distilled water through the column. Its activity is 20 units/g.

Continuous Separation of L-methionine

A solution of 0.1 M N-acetyl-DL-methionine in distilled water, pH 7, containing $5 \times 10^{-4}$ mole/l of Co$^{++}$ ions is passed at a temperature of 55° C. continuously through the column, and at a rate of 60 ml/h.

The conversion rate to L-methionine is determined after 3 hours, and then every 5 days:
  After 3 hours the conversion is 100 mole %
  After 5 days the conversion is 100 mole %
  After 10 days the conversion is 93 mole %
  After 15 days the conversion is 85 mole %
  After 20 days the conversion is 83 mole %
  After 25 days the conversion is 80 mole %
  After 30 days the conversion is 30 mole %

The inflow of N-acetyl-DL-methionine solution is stopped, and replaced by the same solution of L-aminoacylase as above, in which 50 ml of the solution is passed in 20 minutes.

The flow of N-acetyl-DL-methionine solution is restarted as a continuation of the above test.

After 30 days + 3 hours, the conversion is 92 mole %.

After 35 days + 3 hours, the conversion is 87 mole %.

After 40 days + 3 hours, the conversion is 75 mole %.

It can be seen that the column operates well and the support is easily reactivated.

EXAMPLE 4

Continuous Separation of L-phenylalanine

The passage of the N-acetyl-DL-methionine through the column of example 3 is stopped, and a solution of 0.1 M N-acetyl-DL-phenylalanine, in distilled water, pH 7, containing $5 \times 10^{-4}$ mole/l of $Co^{++}$ ions, is passed continuously at a temperature of 55° C. through the said column, at a rate of 60 ml/h.

The conversion rate to L-phenylalanine is determined by the ninhydrin reaction, after 3 hours and then every 5 days added to the above.

After 40 days + 3 hours, the conversion is 62 mole %.

After 45 days + 3 hours, the conversion is 50 mole %.

After 50 days + 3 hours, the conversion is 40 mole %.

After 55 days + 3 hours, the conversion is 30 mole %.

The flow of N-acetyl-DL-phenylalanine solution is stopped and replaced by the same solution of L-aminoacylase as in example 3. 50 ml of the solution are passed in 20 minutes.

The flow of N-acetyl-DL-phenylalanine is recommenced as a continuation of the above.

After 55 days + 3 hours, the conversion is 83 mole %.

After 60 days + 3 hours, the conversion is 80 mole %.

After 65 days + 3 hours, the conversion is 80 mole %.

It may therefore be concluded that the loss of activity is slow and that the support-aminoacylase complex enables N-acetyl-DL-amino-acids to be equally treated.

EXAMPLE 5

Fixation of the Enzyme 100 ml of a 1% by weight solution is distilled water of L-aminoacylase obtained from Aspergillus, and sold under the brand name AMANO (Pharmaceutical Co. Ltd.), is circulated in the form of a closed circuit for 1 hour through a column 0.7 cm in diameter and 34 cm high, containing 13 ml of the same support as that of example 2. The circulation flow rate is 700 ml/h, which creates a pressure of 8 bars in the column. The activity of the complex is 20 units/g.

Continuous Separation of L-methionine Under Pressure

A solution of 0.1 M N-acetyl-DL-methionine, in distilled water, pH 7, containing $5 \times 10^{-4}$ mole/l of $Co^{++}$ ions at ambient temperature, is passed continuously through the column at a flow rate of 700 ml/h, thereby creating a pressure of 8 bars.

The conversion rate to L-methionine is then determined:

After 3 hours, the conversion rate is 20 mole%.

After 24 hours, the conversion rate is 20 mole%.

After 48 hours, the conversion rate is 20 mole%.

It is found that the complex preserves its activity, that there is little aging, and that the support is unaffected by the pressure.

As a comparison, the same test is repeated but the ion-exchange support is a commercial support, namely "QMA Sephadex type A 50", marketed by Pharmacia.

During the fixation of the enzyme an increase in pressure up to 20 bars and a blocking of the column are observed, resulting in zero flow.

The good mechanical properties of the support of the invention are evident, enabling procedures to be carried out without difficulty under very simple conditions.

We claim:

1. Stable support-aminoacylase complexes having an enzymatic activity, consisting of aminoacylase adsorbed on a support in the form of an inorganic porous substance selected from the group consisting of a metal oxide and silica having a grain size between 4 μm and 5 mm, a specific surface of the order of 5 to 150 m$^2$/g, a pore diameter of 500 to 2500 Å, a pore volume of 0.4 to 2 ml/g, and coated in an amount of less than 10 mg/m$^2$ without blocking the pores of the support, with a film of cross-linked polymer containing or bearing groups selected from the group consisting of tertiary amine and quaternary ammonium salts in which the functional groups are from the group consisting essentially of

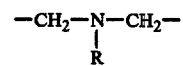

or $-CH_2-N^{(\pm)}(R)_3 X^{(-)}$, in which R, which may be identical or different, represents an alkyl or hydroxyalkyl group having 1 to 4 carbon atoms and X is an inorganic or organic anion.

2. Complexes as claimed in claim 1, in which the metal oxide is selected from the group consisting of titanium oxide and alumina.

3. Complexes as claimed in claim 1, in which the fixed aminoacylase is of animal origin.

4. Complexes as claimed in claim 1, in which the fixed aminoacylase is produced by microorganisms.

5. Complexes as claimed in claim 1 in which X is selected from the group consisting of chloride, sulphate, nitrate, phosphate and citrate.

6. Complexes as claimed in claim 1 in which the coating is a cross-linked polymer present in an amount within the range of 1 to 6 mg/m$^2$.

7. Complexes as claimed in claim 1 in which the coated support has an exchange capacity of less than 2 meq/g.

8. Complexes as claimed in claim 1 in which the coated support has an exchange capacity within the range of 0.3–1.2 meq/g.

* * * * *